(12) United States Patent
Birudaraj et al.

(10) Patent No.: US 7,893,037 B2
(45) Date of Patent: *Feb. 22, 2011

(54) PHARMACEUTICAL COMPOSITION AND PROCESS

(75) Inventors: Kondamraj Birudaraj, Pine Brook, NJ (US); Michael Thomas Brandl, Redwood City, CA (US); Shridhar Hegde, Mountain View, CA (US); Felix Sana, Sunnyvale, CA (US); Dimitrios Stefanidis, Mountain View, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 335 days.

This patent is subject to a terminal disclaimer.

(21) Appl. No.: 12/079,715

(22) Filed: Mar. 28, 2008

(65) Prior Publication Data

US 2008/0260826 A1 Oct. 23, 2008

Related U.S. Application Data

(60) Provisional application No. 60/920,586, filed on Mar. 29, 2007.

(51) Int. Cl.
| | | |
|---|---|---|
| *A01N 43/04* | (2006.01) | |
| *A61K 31/70* | (2006.01) | |
| *A61K 9/14* | (2006.01) | |
| *A61K 9/20* | (2006.01) | |
| *A61K 9/50* | (2006.01) | |

(52) U.S. Cl. .................. 514/49; 424/464; 424/489; 424/499

(58) Field of Classification Search ................ None
See application file for complete search history.

(56) References Cited

U.S. PATENT DOCUMENTS

2007/0202175 A1 8/2007 Ahmed

FOREIGN PATENT DOCUMENTS

| WO | WO 2004/046159 A1 | 6/2004 |
|---|---|---|
| WO | WO 2007/068615 A2 | 6/2007 |
| WO | WO 2007/068615 A3 | 6/2007 |

*Primary Examiner*—Traviss C McIntosh, III
(74) *Attorney, Agent, or Firm*—Brian L. Buckwalter

(57) ABSTRACT

The present invention relates to a method of forming granules of (2R,3S,4R,5R)-5-(4-amino-2-oxo-2H-pyrimidin-1-yl)-2-azido-3,4-bis-iso-butyryloxy-tetrahydro-furan-2-ylmethyl isobutyrate; hydrochloride salt (I), comprising mixing I, with a granulating amount of a granulating liquid, and a polyethylene glycol (PEG)/polypropylene glycol (PPG) block copolymer as a binder and solubility enhancer to form wet granules which are then dried to remove the granulating liquid.

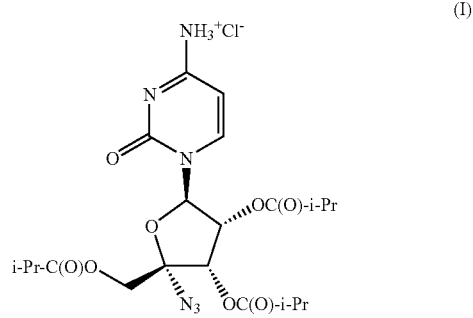

(I)

12 Claims, No Drawings

PHARMACEUTICAL COMPOSITION AND PROCESS

CROSS REFERENCE TO PRIOR APPLICATIONS

This application is claims benefit of U.S. Provisional Application No. 60/920,586, filed Mar. 29, 2007, which is hereby incorporated by reference in its entirety.

FIELD OF THE INVENTION

The present invention relates to a novel compressed tablet formulation having as an active ingredient 4'-azidocytidine-2', 3', 5'-tri-iso-butyrate hydrochloride (I) and a process for preparing the formulation. The composition is useful in the therapy of hepatitis C virus (HCV).

BACKGROUND OF THE INVENTION

Nucleoside derivatives often are potent anti-viral (e.g., HIV, HCV, Herpes simplex, CMV) and anti-cancer chemotherapeutic agents. Unfortunately their utility is often limited by two factors. Firstly, poor pharmacokinetic properties frequently limit the absorption of the nucleoside from the gut and the intracellular concentration of the nucleoside derivatives and, secondly, suboptimal physical properties restrict formulation options which could be employed to enhance delivery of the active ingredient.

Prodrugs (P. Ettmayer et al., *J. Med. Chem.* 2004 47(10): 2393-2404; K. Beaumont et al., *Curr. Drug Metab.* 2003 4:461-485; H. Bundgaard, Design of Prodrugs: Bioreversible derivatives for various functional groups and chemical entities in Design of Prodrugs, H. Bundgaard (ed) Elsevier Science Publishers, Amersterdam 1985; G. M. Pauletti et al. *Adv. Drug Deliv. Rev.* 1997 27:235-256; R. J. Jones and N. Bischofberger, *Antiviral Res.* 1995 27; 1-15 and C. R. Wagner et al., *Med. Res. Rev.* 2000 20:417-45) afford one technique to improve absorption of the drug. Typical examples of prodrugs include compounds that have biologically labile protecting groups linked to a functional moiety of the active compound. Alkylation, acylation or other lipophilic modification of the hydroxy group(s) on the sugar moiety have been utilized in the design of pronucleotides. These pronucleotides can be hydrolyzed or dealkylated in vivo to generate the active compound. Unfortunately many otherwise useful prodrugs exhibit limited aqueous solubility which present a significant formulation challenge.

4-Amino-1-(5-azido-3,4-dihydroxy-5-hydroxymethyl-tetrahydro-furan-2-yl)-1H-pyrimidin-2-one (II) was found to be an useful inhibitor of HCV NS5B polymerase; however, the nucleoside exhibited insufficient bioavailabilty. (2R,3S,4R,5R)-5-(4-amino-2-oxo-2H-pyrimidin-1-yl)-2-azido-3,4-bis-iso-butyryloxy-tetrahydro-furan-2-ylmethyl isobutyrate hydrochloride salt (I) was found to be efficiently absorbed and revert to I in plasma. Unfortunately 1 forms a gel when exposed to water which limits its solubility. The term gel herein refers to a biphasic dispersion containing water and small solid hydrated particles of I. The solid particles dispersed in water are difficult to handle and process into the final dosage form. The gel hinders dissolution of the active ingredient after administration. Thus effective use of I in HCV therapy requires formulation which avoids forming a gel during processing, has suitable pharmaceutical characteristics and dissolves effectively in the gut and produces a solution which can be absorbed from the GI tract. Antiviral therapy further requires relatively large quantities of active ingredient to provide high serum concentrations of the active ingredient to avoid selection pressure for resistant strains. Requiring the tablet to contain high levels of I and limits excipients, carriers and diluents further which can be incorporated and increases the challenge to the formulator to design an acceptable and efficacious formulation.

SUMMARY OF THE INVENTION

The present invention relates to a pharmaceutical composition comprising a compressed tablets containing granules of isobutyric acid (2R,3S,4R,5R)-5-(4-amino-2-oxo-2H-pyrimidin-1-yl)-2-azido-3,4-bis-iso-butyryloxy-tetrahydro-furan-2-ylmethyl ester; hydrochloride salt (I; also referred to herein as 4'-azidocytidine-2', 3', 5'-tri-iso-butyrate hydrochloride) and a polyethylene glycol (PEG)/polypropylene glycol (PPG) block copolymer.

(I)

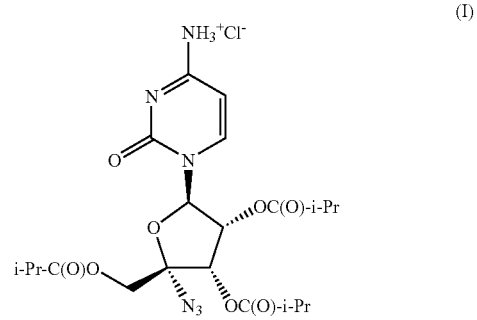

DETAILED DESCRIPTION OF THE INVENTION

The subject invention provides a pharmaceutical composition for orally administering 4'-azidocytidine-2', 3', 5'-tri-iso-butyrate hydrochloride which comprises, based on the total weight of the composition, from about 250 mg to 500 mg of 4'-azidocytidine-2', 3', 5'-tri-iso-butyrate hydrochloride (I). The compound is described and claimed in U.S. Pat. No. 6,846,810 issued Jan. 2, 2005. A process to prepare the parent nucleoside is described by T. C. Connolly et al. in U.S. Publication 20050038240 published Feb. 17, 2005. Both documents are hereby incorporated by reference in their entirety.

The triacylated nucleoside I has been found to decrease the viral load of patients infected with hepatitis C virus (HCV). Hepatitis C virus is the leading cause of chronic liver disease throughout the world (N. Boyer et al., *J Hepatol.* 2000 32:98-112). Patients infected with HCV are at risk of developing cirrhosis of the liver and subsequent hepatocellular carcinoma and hence HCV is the major indication for liver transplantation. Although I is available in crystalline form, it has pH-dependent physicochemical properties. Moreover, the compound readily forms a gel when exposed to water and is difficult to process with aqueous solutions.

Tablets have long been a preferred solid dosing form. Tablets containing drug substances can be prepared by compression or molding techniques and may, or may not, contain additional diluents and/or excipients. Compression of granular ingredients alone or in combination with binders, disintegrants, controlled release polymers, lubricants or diluents is commonly utilized. Granulation is a process whereby granules are formed from a bulk drug substance, with or without excipients, to improve the properties of the bulk drug or formulation. Granules are preparations consisting of solid, dry agglomerates of powder particles sufficiently robust to withstand processing.

Granular active ingredients are commonly prepared by wet granulation, fluid bed granulation or dry granulation. Wet granulation is distinguished from dry granulation in that a granulating liquid, such as water, organic liquids or mixtures thereof, are used in processing to produce granules. The advantages of wet granulation include improvement of the cohesiveness and compactability of powders, increase in density, good distribution providing uniform content of micronized or finely milled low-dosage drugs, reduction of dust and airborne contamination, and prevention of segregation of components. Good granules typically have few fines, uniform size and stay intact after drying and sizing. Sizing may be accomplished by a sieve or mill, for instance. While the tablets in the invention described herein are produced by wet granulation, one skilled in the art will appreciate that the other granulation techniques could be utilized and are within the scope of the invention.

While surfactants can be incorporated to enhance solubility and dispersability of the active ingredient, the added surfactants, an other excipients, must produce a tablet which has acceptable characteristics such as cohesiveness and compactability of powders, acceptable density, hardness, good distribution providing uniform content, reduction of dust and airborne contamination, and prevention of segregation of components. Thus a task of finding an acceptable formulation can afford a significant challenge to the formulator.

Wet agglomeration has traditionally been an empirical art wherein prediction and explanation of the observed behavior has been difficult (S. Iveson et al. *Powder Technol.* 2001 117:3-39). A critical aspect of developing a satisfactory wet granulation formulation is identifying a binder which effectively coats the powdered drug and promotes aggregation or agglomeration of the particles into larger granules with optimal size and shape, improved flowability and acceptable dissolution rate, granule strength and bulk density. The skilled worker often makes a subjective determination by observing the consistency of the granules.

During binder aggregation, a solution of a liquid binder is poured, sprayed or atomized onto an agitated bed of powder contained in a mixer which imparts shearing forces to the powdered mass. Equipment for wet granulation is well know in the art. (E. Rudnic and J. B. Schwartz. Oral Solid Dosage Forms. In *Remington: The Science and Practice of Pharmacy,* 19$^{th}$ edition; A. R. Gennaro, Ed.; Mack Publishing Co: Easton Pa., 1995, Volume II, pp. 1615-1660)

It has now surprisingly been found that wet granulation of I with polyethylene glycol (PEG)/polypropylene glycol (PPG) block copolymers provide an acceptable granular product in which the block copolymer is a binder which provides for coalescence of particles without formation gel and the copolymer that promotes dissolution of I and improves bioavailability. A further advantage of compressed tablets prepared from the wet granules is that the amount of active ingredient can comprise a larger portion of the pharmaceutical composition.

The term "block copolymer" as used herein refers to a copolymer comprised of 2 or more blocks (or segments) of different homopolymers. The term homopolymer refers to a polymer comprised of a single monomer. Many variations of block copolymers are possible including simple diblock polymers with an A-B architecture and triblock polymers with A-B-A or A-B-C architectures. Poloxomers (or LUTROL®) are A-B-A block copolymers in which the A segment is a hydrophilic polyethylene glycol homopolymer and the B segment is hydrophobic polypropylene glycol homopolymer. Poloxomers are commercially available from BASF Corporation. Depending on the relative size of the blocks the copolymer can be a solid, liquid or paste. LUTROL® is a trademark for poloxomers. The terms poloxomer and LUTROL® are used interchangeably herein. Poloxomer 188 has an average molecular weight of about 8600 melting point of 52°-54° C. and HLB (hydrophilic-lipophilic balance) of 18-29 and the average particle size ranging from 1 micron to 500 microns. The polyoxyethylene units represent about 81% of the molecular weight. Poloxomer 188 is readily soluble in water. In the HCV prodrug formulation the block copolymer limits exposure to moisture which causes undesirable gelling of the AI. Other solid carriers which could be used to produce solid dispersions of I include Vitamin E TPGS (Eastman Kodak), Gelucire 44/14, Gelucire 50/13 (Gattefosse, N.J.), Solutol HS15, poloxamer 407, LUTROL F77, Cremophor RH40 (BASF, NJ), sucrose dipalmitate and sucrose distearate (Croda, N.J.).

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The term "optional" or "optionally" as used herein means that a subsequently described event or circumstance may, but need not, occur, and that the description includes instances where the event or circumstance occurs and instances in which it does not.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or". As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In first embodiment of the present invention there is provided a pharmaceutical composition comprising granules of isobutyric acid (2R,3S,4R,5R)-5-(4-amino-2-oxo-2H-pyrimidin-1-yl)-2-azido-3,4-bis-iso-butyryloxy-tetrahydro-furan-2-ylmethyl ester hydrochloride salt (I) and a polyethylene glycol (PEG)/polypropylene glycol (PPG) block copolymer In a second embodiment of the present invention there is provided a pharmaceutical composition comprising granules of I, a polyethylene glycol (PEG)/polypropylene glycol (PPG) block copolymer and at least one diluent, carrier and/or excipient.

In a third embodiment of the present invention there is provided a pharmaceutical composition comprising granules of I and a poloxomer.

In a fourth embodiment of the present invention there is provided a pharmaceutical composition comprising granules of I and a poloxomer and further comprising at least one diluent, carrier and/or excipient.

In a fifth embodiment of the present invention there is provided a pharmaceutical composition comprising granules of I and poloxomer 188.

In a sixth embodiment of the present invention there is provided a pharmaceutical composition comprising granules of I and a poloxomer 188 wherein the granules are produced utilizing a wet granulation technique.

In a seventh embodiment of the present invention there is provided a pharmaceutical composition comprising granules of I and poloxomer 188 wherein said granules comprise 5-20% (wt/wt) of poloxomer 188.

In an eighth another embodiment of the present invention there is provided a pharmaceutical composition in a compressed table comprising granules of I, poloxomer 188 wherein said granules comprise 5-20% (wt/wt) of poloxomer 188 and optionally comprising at least one diluent, a disintegrant, a lubricant and a coating material.

In a ninth embodiment of the present invention there is provided a pharmaceutical composition in a compressed table comprising granules of I, poloxomer 188 wherein said granules comprise 5-20% (wt/wt respect to I) of poloxomer 188, mannitol, microcrystalline cellulose, croscarmellose and magnesium stearate.

In a tenth embodiment of the present invention there is provided a pharmaceutical composition in a compressed table comprising granules containing 50-70% by weight of 1, 2-8% by weight of poloxomer 188, 2-20% by weight mannitol, 5-30% by weight microcrystalline cellulose, 3-20% by weight croscarmellose and 0.3-2% by weight magnesium stearate and optionally coated with polymeric coating systems known in the art including, but not limited to HPMC (hydroxypropyl methylcellulose), PVA (polyvinyl alcohol) or copolymers such as, but not limited to, PVP (polyvinylpyrrolidine). Optionally the formulation can include plasticizers, coloring agents and glidants. The total weight of the compressed tablet is between 100 and 1200 mg.

In an eleventh embodiment of the present invention there is provided a pharmaceutical composition in a compressed table comprising granules containing 55-65% by weight of isobutyric acid (2R,3S,4R,5R)-5-(4-amino-2-oxo-2H-pyrimidin-1-yl)-2-azido-3,4-bis-iso-butyryloxy-tetrahydro-furan-2-yl-methyl ester hydrochloride salt (1), 5-7% by weight of poloxomer 188, 3-7% by weight mannitol, 15-25% by weight microcrystalline cellulose, 8-12% by weight croscarmellose and 1.2-1.8% by weight magnesium stearate and optionally coated with polymeric coating systems known in the art including, but not limited to HPMC, PVA, polyvinyl alcohol or copolymers such as, but not limited to, PVP. Optionally the formulation can include plasticizers, coloring agents and glidants. The total weight of the compressed tablet is between 100 and 1200 mg.

In a tenth embodiment of the present invention there is provided a pharmaceutical composition in a compressed table comprising granules containing 50-70% by weight of 1, 2-8% by weight of poloxomer 188, 2-20% by weight mannitol, 5-30% by weight microcrystalline cellulose, 3-20% by weight croscarmellose and 0.3-2% by weight magnesium stearate and optionally coated with polymeric coating systems known in the art including, but not limited to HPMC (hydroxypropyl methylcellulose), PVA (polyvinyl alcohol) or copolymers such as, but not limited to, PVP (polyvinylpyrrolidine). Optionally the formulation can include plasticizers, coloring agents and glidants. The total weight of the compressed tablet is between 500 and 1000 mg.

The term excipients as used herein refers to inert materials which impart satisfactory processing and compression characteristics into the formulation or impart desired physical characteristics to the finished table.

Diluents are inert ingredients added to adjust the bulk in order to produce a size practical for compression. Common diluents include dicalcium phosphate, calcium sulfate, lactose, cellulose, kaolin, mannitol, sodium chloride starch and powdered sugar. Diluents such as mannitol, lactose, sorbitol, sucrose and inositol in sufficient quantities aid disintegration of the tablet and are frequently used in chewable tablets. Microcrystalline cellulose (AVICEL®) has been used as an excipient in direct compression formula.

Binders are added to powders to impart cohesive qualities to the powder which allows the compressed tablet to retain its integrity. Materials commonly used as binders include starch, gelatin and sugars such as sucrose, glucose, dextrose, molasses and lactose. Natural and synthetic gums including acacia, sodium alginate, panwar gum, ghatti gum, carboxymethyl cellulose, methyl cellulose, polyvinylpyrrolidone, ethyl cellulose have also be used binders in some formulations.

Lubricants are employed to prevent adhesion of the tablet material to the surface of dyes and punches. Commonly used lubricants include talc, magnesium stearate, calcium stearate, stearic acid, hydrogenated vegetable oils and PEG. Water soluble lubricants include sodium benzoate, mixtures of sodium benzoate and sodium acetate, sodium chloride, leucine and Carbowax 4000.

Glidants are incorporated to improve the flow characteristics of the tablet powder. Colloidal silicon dioxide (AEROSIL®) is a common glidant. Talc may serve as a combined lubricant/glidant.

A disintegrant is a substance, or a mixture of substances added to facilitate breakup or disintegrate after administration. Dried and powdered corn starch or potato starch are popular disintegrants. They have a high affinity for water and swell when moistened leading to rupture of the tablet. A group of materials known as super-disintegrants include croscarmelose, a cross-linked cellulose, crosprovidone, a cross-linked polymer and sodium starch glycolate, a cross-linked starch. Croscarmellose (USP-NF) is a cross-linked carboxymethylcellulose sodium.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof. The skilled pharmaceutical chemist will be aware of excipients, diluents and carriers which can be used interchangeably and these variations do not depart from the spirit of the invention.

Example 1

Compressed Tablet Prepared by Wet Granulation

| Ingredient | mg/tablet |
| --- | --- |
| Compound I | 537 |
| poloxamer 188 (LUTROL micro 68 MP) | 53.7 |
| silicified microcrystalline cellulose (Prosolve 90HD) | 161.05 |
| mannitol (Partech M200) | 44.8 |
| croscarmellose sodium (Ac-Di-SOL) | 89.5 |
| magnesium stearate | 8.95 |
| Opadry Yellow 03K 12429 | 27 |

Example 2

Process for Preparing the Compressed Tablets

Preparation of Kernals
- (a) Prepare a 30% (w/w) solution of Poloxomer 188 by slowly adding the poloxomer to sterile water for irrigation or injection agitated with propeller mixer.
- (b) Place I into a high shear granulator and with the impeller and chopper blades running at low to medium speed, spray the poloxomer solution onto the powder. Additional sterile water may be added until an optimal granulation is obtained that can be converted into a solid dosage form.
- (c) Dry the wet granules in a forced air oven set at 50°±5° C. for at least 15 h or until the water content of the granulation is less than about 1.5% on a moisture balance set at 90° C.
- (d) Mill the dried granulation to an acceptable particle size range (100 to 1300 microns) for tableting.
- (e) Place the milled granular powder in a blender, add mannitol, croscarmellose sodium and silicified microcrystalline cellulose and blend for 15 min or until a homogenous powder is obtained.
- (f) To the blended powder from step 5 add magnesium stearate which was passed through a #30 mesh screen and blend for 5 min.
- (g) Compress the granulation in a suitable table press.

Film Coating Procedure
- (a) Disperse Opadry in water by mixing gently to avoid air entrapment.
- (b) Place the kernels into a perforated coating pan and preheat the tablets in a range of 25 to 70° C. with intermittent jogging.
- (c) Spray the heated kernels with the stirred Opadry dispersion with an air spray system until there is about 4% weight gain.
- (d) Reduce the inlet air temperature and dry the coated tablets by jogging until the moisture content of the tablets, determined by loss on drying in a moisture balance set at 90° C. is less than 2.0%.
- (e) Cool the tablets to RT and store in a suitable container.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A pharmaceutical composition comprising granules containing isobutyric acid (2R,3S,4R,5R)-5-(4-amino-2-oxo-2H-pyrimidin-1-yl)-2-azido-3,4-bis-iso-butyryloxy-tetrahydro-furan-2-ylmethyl ester hydrochloride salt (I) and a polyethylene glycol (PEG)/polypropylene glycol (PPG) block copolymer.

2. A composition according to claim 1 further comprising at least one diluent, carrier and/or excipient.

3. A pharmaceutical composition according to claim 1 wherein said PEG/PPG block copolymer is a poloxomer.

4. A pharmaceutical composition according to claim 3 further comprising at least one diluent, carrier and/or excipient.

5. A pharmaceutical composition according to claim 4 wherein said granules comprise I and poloxomer 188.

6. A pharmaceutical composition according to claim 5 wherein the granules are produced by a wet granulation technique.

7. A pharmaceutical composition according to claim 5 wherein said granules comprise 5-20% (weight/weight) poloxomer 188.

8. A pharmaceutical composition according to claim 7 wherein said granules are formed into a compressed tablet said tablet further optionally comprising at least one diluent, a disintegrant, a lubricant and a coating material.

9. A pharmaceutical composition according to claim 8 wherein said diluents are mannitol an optionally MCC, said disintegrant is croscarmellose and said lubricant is magnesium stearate.

10. A pharmaceutical composition according to claim 9 wherein said compressed tablet comprises:

| Ingredient | % composition by weight |
| --- | --- |
| Compound I | 50-70 |
| poloxamer 188 | 2-8 |
| silicified microcrystalline cellulose | 5-30 |
| mannitol | 2-20 |
| croscarmellose sodium | 3-20 |
| magnesium stearate | 0.3-2 | wherein said compressed tablet is optionally coated with Opadry yellow 03K 12429 and the total weight of said compressed tablet is from 100 to 1200 mg.

11. A pharmaceutical composition according to claim 8 wherein said compressed tablet comprises:

| Ingredient | % composition by weight |
|---|---|
| Compound I | 55-65 |
| poloxamer 188 | 5-7 |
| silicified microcrystalline cellulose | 15-25 |
| mannitol | 3-7 |
| croscarmellose sodium | 8-12 |
| magnesium stearate | 1.2-1.8. | wherein said compressed tablet is optionally coated with Opadry yellow 03K 12429 and the total weight of said compressed tablet is from 100 to 1200 mg.

12. A pharmaceutical composition according to claim 10 wherein the total weight of said compressed tablet is 500 to 1000 mg.

* * * * *